(12) United States Patent
Enzinger

(10) Patent No.: US 6,516,803 B1
(45) Date of Patent: Feb. 11, 2003

(54) DEVICE FOR REMOVING SPUTUM FROM A TRACHEAL CATHETER

(76) Inventor: Alfred Enzinger, Pachelbelstrasse 86, D-90469 Nürnberg (DE)

( * ) Notice: Subject to any disclaimer, the term of this patent is extended or adjusted under 35 U.S.C. 154(b) by 0 days.

(21) Appl. No.: 09/720,661
(22) PCT Filed: Nov. 26, 1998
(86) PCT No.: PCT/DE98/03473
§ 371 (c)(1), (2), (4) Date: Dec. 28, 2000
(87) PCT Pub. No.: WO00/00246
PCT Pub. Date: Jan. 6, 2000

(30) Foreign Application Priority Data

Jun. 28, 1998 (DE) .......................................... 298 11 374
Aug. 24, 1998 (DE) .......................................... 198 38 370

(51) Int. Cl.[7] ............................................. A61M 16/00
(52) U.S. Cl. .............. 128/207.16; 128/912; 128/202.27
(58) Field of Search ....................... 128/207.16, 202.27, 128/205.19, 206.22, 205.12, 911, 912; 604/523, 533, 534, 535, 536, 537, 538, 187, 207, 208, 218, 231, 236, 93.01; 600/432

(56) References Cited

U.S. PATENT DOCUMENTS

| 3,603,313 A | | 9/1971 | Arblaster ..................... 128/275 |
|---|---|---|---|
| 4,668,215 A | * | 5/1987 | Allgood ....................... 604/236 |
| 5,255,676 A | * | 10/1993 | Russo ..................... 128/205.24 |
| 5,343,857 A | * | 9/1994 | Schneider et al. ..... 128/200.23 |
| 5,349,950 A | * | 9/1994 | Ulrich et al. ........... 128/207.14 |
| 5,433,195 A | | 7/1995 | Kee et al. ............... 128/207.14 |
| 5,598,840 A | * | 2/1997 | Iund et al. .............. 128/202.27 |
| 5,735,271 A | * | 4/1998 | Lorenzen et al. ....... 128/200.26 |
| 5,765,557 A | | 6/1998 | Warters .................. 128/207.14 |
| 5,919,174 A | * | 7/1999 | Hanson ....................... 251/320 |
| 6,070,582 A | * | 6/2000 | Kee ....................... 128/207.16 |
| 6,227,197 B1 | * | 5/2001 | Fitzgerald .............. 128/200.26 |
| 6,227,200 B1 | * | 5/2001 | Crump et al. .......... 128/207.14 |

* cited by examiner

Primary Examiner—Aaron J. Lewis
Assistant Examiner—Mital Patel
(74) Attorney, Agent, or Firm—Venable; Norman N. Kunitz

(57) ABSTRACT

A device for removing sputum from a tracheal catheter inserted into the trachea of a patient. The aim of the invention is to supplement existing tracheal catheters in such a way that sputum is automatically kept away from the air filter and is removed without any problems so that excruciating and painful choking attacks in patients can be prevented and the risk of death by asphyxia is eliminated. This is achieved by a housing (4) having a first orifice (1) that can be attached to the end of the tracheal catheter projecting from the trachea; a second orifice (2) for exhaled air-filtered fresh air exchange and a third orifice (3) for sputum outflow.

9 Claims, 1 Drawing Sheet

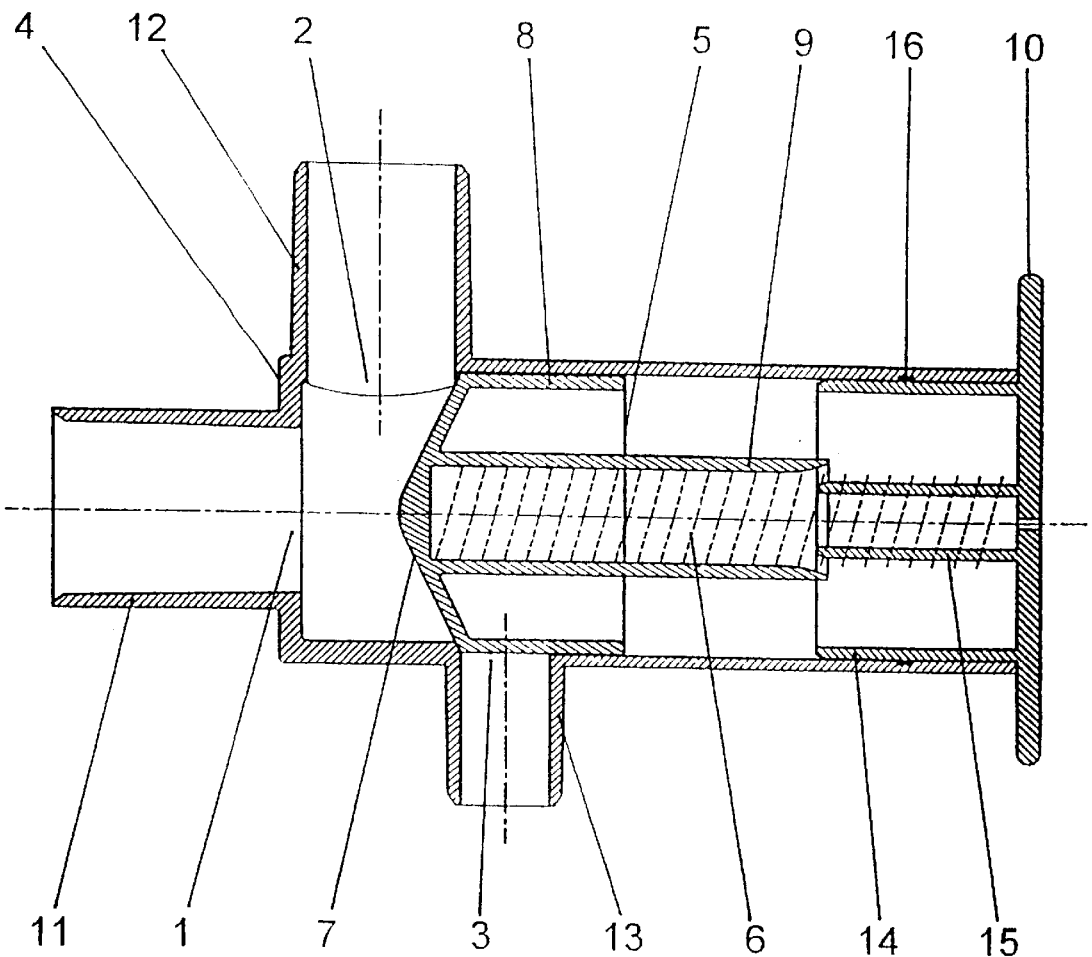

DEVICE FOR REMOVING SPUTUM FROM A TRACHEAL CATHETER

BACKGROUND OF THE INVENTION

The invention relates to a device for removing sputum (expectoration coughed up from the respiratory organs) from a tracheal catheter inserted into the trachea of a patient.

From U.S. Pat. No. 5,765,557 it is known that an increased amount of sputum collects in the lungs of patients having a tracheal catheter inserted into the trachea, which must be removed through regular suction. However, this known technique is extremely disadvantageous and considerably increases the danger of infections. The aforementioned US Patent therefore also provides for an airflow control device inside the patient in order to facilitate the removal of sputum from the patient's inside without suctioning. The device contains a tubular duct that can be inserted into the patient and comprises a path for the inhalation as well as a separate path for the exhalation of air. The device further comprises an airflow control device on the inside, which is designed to control the air flowing in through the intake path for expanding the lungs of the patient and to permit the air that must be exhaled to flow through a separate exhalation path. The device is designed to remove the sputum for the patient by way of this exhalation path and the force of the air exhaled from of the lung.

The airflow control device, which is installed inside the patient, cannot be monitored from the outside, so that its error-free operation can only be assumed. Help needed during a malfunction frequently comes too late. For that reason, the device is not widely used in practical applications.

In practical operations, a tracheal catheter known from German Application 35 24 126 A1 therefore continues to be used in place of this device. The frontal end of this tracheal catheter can be inserted into the trachea, for example by making a cut in the trachea while a connecting piece that projects from the trachea is fitted onto the back end. For example, an air hose can be fitted onto this connecting piece for form a connection to a respirator or an air filter through which the patient is supplied with filtered, meaning germ-free respiratory air.

However, it has turned out that the cough frequently is so strong that the inserted air filter is clogged with sputum within a short time, often after less than ten minutes, such that the patient is gasping for air and must fight an asphyxia attack unless the filter is removed immediately and replaced with a new one. Since the patients are frequently paralyzed, for example by a stroke or brain seizure, they cannot remove the filter themselves, but depend on help from the nursing staff. As a result of the known shortage of nursing staff, patients frequently must depend on additional help from relatives and acquaintances. In reality, the filter is often simply omitted because staff does not have the time to replace it constantly. The patient then breathes in unfiltered air, which strongly increases the danger of contracting dangerous or even deadly infections.

SUMMARY OF THE INVENTION

It is the object of the invention to improve the known tracheal catheter, such that the sputum is automatically kept away from the air filter and can be removed without problems to avoid painful and agonizing asphyxia attacks by patients, as well as ban the danger of dying from asphyxia, even if the patient is left alone for a longer period of time, e.g. for several hours.

This object generally is solved according to the present invention by a housing with a first opening, which can be connected to the tracheal catheter end that projects from the trachea;

with a second opening for exchanging exhaled air against filtered fresh air and with a third opening for draining the sputum.

One advantageous modification of the invention provides a valve controlled by the respiratory air, which opens the third opening during the exhalation to allow sputum to drain out and closes this opening during the inhalation. It is advantageous if the housing is shaped like a cylinder, wherein the first opening is located in the bottom of the cylinder and the second and third openings are respectively located in its shell surface, essentially opposite each other, and the openings are provided with cylinder-shaped connecting pieces.

In order to connect the device to the tracheal catheter and to other apparatuses, it is furthermore provided that the inside wall of the connecting piece of the first opening has a conical shape and can be fitted onto the tracheal catheter end that projects from the trachea. The connecting piece of the second opening, which preferably points upward in the operating state, has a conical outside wall onto which an air filter for the inhaled air can be fitted. The connecting piece of the third opening, which preferably points downward in the operating state, has a conical outside wall onto which a catch bag for catching the sputum or a hose for draining the sputum to a catch bag can be fitted.

In the simplest case, the valve for opening and closing the third opening is realized as a pivoting flap that is controlled by the respiratory air, which flap opens the third opening during the exhalation, owing to the pressure of the exhaled air and counter to the pressure of a spring, its own weight or an additional weight, so that the sputum can flow out. This valve closes during the inhalation owing to the pressure of the spring, its internal weight or an additional weight.

According to another alternative for opening and closing the third opening, the valve is a piston controlled by the respiratory air. The valve opens the third opening during the exhalation for sputum to drain out, that is to say against the pressure of the exhaled air and against the pressure of a spring, its own weight, or an additional weight. During the inhalation, this opening is closed as a result of the pressure exerted by the spring, its own weight or an additional weight.

Further advantageous embodiments of the invention are mentioned in the additional dependent claims.

The advantages achieved with the invention in particular are that the sputum is automatically kept away from the air filter and can be removed without problems. Thus, the patient is spared painful attacks of asphyxia, and the danger of death by asphyxia is banned. The trouble-free operation of this device can be monitored at any time and at a glance, so that help can be rendered quickly in case of a possible malfunction.

The exemplary embodiment of the invention is shown in the drawing and is described in further detail below.

BRIEF DESCRIPTION OF THE DRAWINGS

The FIGURE is a sectional view of the device according to the invention.

DESCRIPTION OF THE PREFERRED EMBODIMENTS

The device according to the invention comprises a housing 4 in the shape of a cylinder, having a symmetry axis that extends preferably horizontal in the use position. A first opening 1 is arranged in the bottom of the cylinder while two additional openings 2, 3 are respectively arranged in the shell. All three openings 1, 2, 3 are provided with cylinder-shaped connecting pieces 11, 12, 13.

The inside wall of the connecting piece 11 of the first opening 1 has a conical shape, so that this connecting piece 11 can be fitted onto the tracheal catheter end that projects from the trachea. The connecting piece 12 for the second opening 2, which preferably points upward in the position of use, has a conical outside wall onto which an air filter can be fitted for cleaning and decontaminating the inhaled air. The connecting piece 13 in the third opening 3, which preferably points downward in the position of use, has a conical outside wall onto which a bag for catching the sputum or a hose for draining the sputum to such a catch bag can be fitted.

The valve for opening and closing the third opening 3 is realized as a pivotable piston 5 that is controlled by the respiratory air and has a cone-shaped bottom surface 7 and a cylindrical shell 8. The piston is positioned coaxial and such that it can glide easily inside a cylindrical housing 4. In the closed state, the shell 8 covers the third opening 3.

A coaxially extending cylindrical tube 9 is integrally formed onto the inside of the cylinder-shaped shell 8 for piston 5 and accommodates a large portion of a spring 6, designed as helical spring. The other part of this spring is supported by a closing plate 10, which covers a fourth opening in the cylindrical housing 4, on the side opposite the first opening 1. Two cylindrical tubes 14, 15, arranged coaxial to each other, are integrally formed onto the closing plate 10. The outer tube 14 in this case can be inserted into the housing 4 while making contact with the inside wall of housing 4 and can be snapped into an inside wall groove 16, whereas the inner tube 15 engages as a guide into the spring 6.

The movement of piston 5 is controlled by the respiratory air and in cooperation with the spring 6, such that during the exhalation the piston is displaced in the direction of the fourth opening by the pressure of the exhaled air and counter to the slight pressure exerted by spring 6. As a result, it frees the third opening 3 that is covered by the cylindrical shell and points downward when in the use position, so that sputum can drain out. During the inhalation, the piston 5 is moved in the opposite direction as a result of the pressure from spring 6 and the lack of counter pressure by the respiratory air and closes off the third opening 3 once more, so that no unfiltered air can be inhaled via this opening. The respiratory air flows during each phase of this operation only through the second opening 2 and through the air filter that is fitted onto the connecting piece 12.

The cylindrical housing 4 with its connecting pieces 11, 12, 13 and/or the parts 5, 6, 7, 8, 9, 10, 14, 15, 16 arranged on the inside, should advantageously be produced at least in part of plastic, preferably of a transparent plastic, so that the course of the sputum inside the housing can be checked at any time to allow for a timely intervention if, contrary to expectations, the free piston movement is obstructed by more solid components of the sputum.

The trouble-free operation with a prototype of the device was tested by the inventor of the present invention over a longer period of time on a patient paralyzed by a stroke, who was close to the inventor. The testing was carried out under the supervision of physicians and the nursing staff. In the process, it turned out that the device did not require cleaning over a period of several days. Without this device, on the other hand, the clogged air filter must be replaced in acute cases every ten to 15 minutes on the average. The device was extremely well received by the physicians as well as the nursing staff. Using this device in all intensive care stations and in rehabilitation centers is thus urged for humanitarian reasons.

What is claimed is:

1. A device for removing sputum from a tracheal catheter that is inserted into the trachea of a patient, said device comprising a cylindrical housing with a first opening inserted into a base of the cylinder, which can be connected to the tracheal catheter end that projects from the trachea, with a second opening for exchanging exhaled air against filtered fresh air and with a third opening, arranged in a shell of the cylinder, for removing the sputum, wherein the cylindrical housing is made of a transparent material and contains, on an inside, a valve consisting of a piston controlled by respiratory air that opens, during the exhalation, the third opening, preferably downward pointing during use, as a result of the pressure exerted by the exhaled air and counter to the pressure of a spring, its own weight or an additional weight for draining the sputum and which closes the third opening during the inhalation owing to the pressure of the spring, its own weight or an additional weight, said piston having a cone-shaped base and a cylindrical shell, is positioned coaxial and such that it can glide easily inside the cylindrical housing and with its shell surface covers the third opening in a closed condition, while the second opening, which preferably points upward in the use position and is arranged in the cylindrical shell of the cylinder, is always open and is connected to the first opening for a free flow of respiratory air.

2. A device according to claim 1, wherein the first, second and third openings are provided with cylinder-shaped connecting pieces.

3. A device according to claim 2, wherein an inside wall of the connecting piece for the first opening has a conical shape and can be fitted onto the tracheal catheter end that projects from the trachea.

4. A device according to claim 2, wherein the cylinder-shaped connecting piece for the second opening has a conical outside wall for fitting on an air filter for the air to be inhaled.

5. A device according to claim 2, wherein the cylinder-shaped connecting piece for the third opening has a conical outside wall for fitting on a bag, designed to catch the sputum, or a hose for draining the sputum to a catch bag designed to catch the sputum.

6. A device according to claim 1, wherein a coaxially extending cylindrical tube is integrally formed onto an inside surface of the cylindrical shell for the piston, which tube accommodates the spring that is designed as a helical spring.

7. A device according to claim 1, wherein the cylindrical housing is provided with a fourth opening opposite the first opening, which fourth opening can be closed off with a plate, said plate having two integrally formed-on, cylinder-shaped tubes that are arranged coaxial to each other, an outer of said cylinder-shaped tubes can be inserted while making contact with the housing inside wall and can be snapped into an inside wall groove while an inner of said cylinder-shaped tubes engages in the spring that is designed as helical spring and functions as a guide.

8. A device according to claim 1, wherein at least one of the housing with its connecting pieces and parts arranged inside the housing are at least in part made of a plastic.

9. A device according to claim 8, wherein the plastic is a transparent plastic.

* * * * *